United States Patent
Fukui et al.

(10) Patent No.: US 8,765,158 B2
(45) Date of Patent: Jul. 1, 2014

(54) W/O EMULSION COSMETIC

(75) Inventors: Takashi Fukui, Tokyo (JP); Takashi Kawata, Tokyo (JP); Mio Ishita, Tokyo (JP)

(73) Assignee: Kao Corporation, Tokyo (JP)

( * ) Notice: Subject to any disclaimer, the term of this patent is extended or adjusted under 35 U.S.C. 154(b) by 7 days.

(21) Appl. No.: 13/480,570

(22) Filed: May 25, 2012

(65) Prior Publication Data

US 2012/0301523 A1 Nov. 29, 2012

Related U.S. Application Data

(63) Continuation of application No. PCT/JP2010/071046, filed on Nov. 25, 2010.

(30) Foreign Application Priority Data

Nov. 25, 2009 (JP) .................................. 2009-267496

(51) Int. Cl.
*A61K 8/06* (2006.01)
*A61Q 17/04* (2006.01)

(52) U.S. Cl.
USPC ............................................ 424/401; 424/59

(58) Field of Classification Search
USPC .................................................. 424/401, 59
See application file for complete search history.

(56) References Cited

U.S. PATENT DOCUMENTS

2008/0112914 A1 * 5/2008 Cho et al. .................... 424/70.22

FOREIGN PATENT DOCUMENTS

| CN | 1964690 A | | 5/2007 |
|---|---|---|---|
| CN | 101460135 A | | 6/2009 |
| EP | 2 027 847 | | 2/2009 |
| JP | 2001-181136 | | 7/2001 |
| JP | 2005-002076 | | 1/2005 |
| JP | 2005-002077 | | 1/2005 |
| JP | 2005-002078 | | 1/2005 |
| JP | 2005002078 | * | 6/2005 |
| JP | 2009-269866 | | 11/2009 |
| JP | 2011-111402 | | 6/2011 |
| WO | WO 2007/138750 A1 | | 12/2007 |

OTHER PUBLICATIONS

U.S. Appl. No. 13/480,581, filed May 25, 2012, Fukui, et al.
U.S. Appl. No. 13/508,392, filed May 7, 2012, Yamada, et al.
U.S. Appl. No. 13/505,558, filed May 2, 2012, Yamada, et al.
International Search Report issued Mar. 1, 2011, in PCT/JP2010/071046.
English Translation of Written Opinion of International Searching Authority issued Jun. 14, 2012 in PCT/JP2010/071046.

* cited by examiner

*Primary Examiner* — Janet Epps-Smith
*Assistant Examiner* — Courtney Brown
(74) *Attorney, Agent, or Firm* — Oblon, Spivak, McClelland, Maier & Neustadt, L.L.P.

(57) ABSTRACT

A cosmetic composition in the form of a W/O emulsion includes: (A) 1 to 20% by weight of a plate-like powder which has been surface-treated with an alkylalkoxysilane; (B) 0.1 to 10% by weight of an oil that is solid at temperature of 25° C.; (C) 0.5 to 60% by weight of an oil selected from the group consisting of a hydrocarbon oil, an ester oil, and an ether oil, having a viscosity at 25° C. of 500,000 mPa·s or less; and (D) water, wherein a weight ratio of the component (B) to the component (A), (B)/(A), is 0.01 to 5.

20 Claims, No Drawings

W/O EMULSION COSMETIC

CROSS REFERENCES TO RELATED APPLICATIONS

The application is a continuation of International Patent Application No. PCT/JP2010/071046, filed on Nov. 25, 2010, and claims priority to Japanese Patent Application No. 2009-267496, filed on Nov. 25, 2009, all of which are incorporated herein by reference in their entireties.

BACKGROUND OF THE INVENTION

1. Field of the Invention

The present invention relates to a W/O emulsified cosmetic composition.

2. Discussion of the Background

Conventionally, in order to shield ultraviolet rays, an organic ultraviolet ray absorber which efficiently absorbs ultraviolet rays and an ultraviolet ray protective powder which scatters ultraviolet rays are used. For the ultraviolet protective powder, titanium dioxide and zinc oxide are frequently used. However, in order to shield ultraviolet rays, a large amount of such substances needs to be mixed in cosmetic compositions. Therefore, when the cosmetic compositions are applied to the skin, the skin appears white, a dryness specific to powders is experienced, and a feeling to the touch is bad.

In order to suppress such a dry feeling when the cosmetic composition is applied to skin, for example, cosmetic compositions have been proposed employing pigment that is surface-treated to reduce oil absorption, thus minimizing degreasing of sebum from skin, and improving durability of the makeup, water resistance, sebum resistance, texture, ability to avoid transfer of makeup after application, and coloring, while decreasing the burden on the skin. Such compositions are proposed, for example, in Japanese Patent Application Laid-Open (JP-A) 2005-2076, JP-A 2005-2077, and JP-A 2005-2078.

However, even if pigment which has been subjected to surface treatment is used, dryness cannot be sufficiently suppressed, and a high moisture retaining property cannot be obtained.

SUMMARY OF THE INVENTION

In embodiments of the present invention, cosmetic compositions may include the following components (A), (B), (C) and (D):

(A) 1 to 20% by weight of a plate-like powder that has been surface-treated with an alkylalkoxysilane;

(B) 0.1 to 10% by weight of an oil that is solid at a temperature of 25° C.;

(C) 0.5 to 60% by weight of an oil selected from the group consisting of a hydrocarbon oil, an ester oil, and an ether oil, each having a viscosity at 25° C. of 500,000 mPa·s or less; and (D) water, wherein a weight ratio of component (B) to component (A), (B)/(A), is 0.01 to 5, and the composition is the form of a W/O emulsion.

Exemplary W/O emulsified cosmetic compositions according to the present invention provide a uniform, smooth coating with high occlusive properties, have an excellent moisture retaining property, and offer a favorable feeling upon use. In addition, exemplary W/O emulsified cosmetic compositions have a high ultraviolet ray protective effect.

DETAILED DESCRIPTION OF THE PREFERRED EMBODIMENTS

Other features of the invention will become apparent in the course of the following descriptions of exemplary embodiments which are given for illustration of the invention and are not intended to be limiting thereof.

Exemplary cosmetic compositions according to the present invention do not cause a dry feeling when applied to skin, have an excellent moisture-retaining property, and have a high ultraviolet protective effect.

The present inventors have found that by using certain amounts of a plate-like powder substance that has been surface-treated with an alkylalkoxysilane and an oil that is solid at a temperature of 25° C., it is possible to obtain a W/O emulsified cosmetic composition which forms a coating with high occlusive properties on the surface of the skin, has an excellent moisture retaining property, and provides a good feeling upon use, as well as which has a high ultraviolet ray protective effect.

In embodiments, component (A) in cosmetic compositions according to the present invention is a plate-like powder that has been surface-treated with an alkylalkoxysilane, and among these, a flaky powder having an average particle diameter of 0.1 to 10 μm, preferably 0.2 to 1 μm, and having a plate ratio (average particle diameter/thickness) of 3 or more, preferably 5 to 45, more preferably 10 to 45, is preferable. The average particle diameter is represented by an arithmetic mean of the major axis and the minor axis of the plate-like smooth surface, and is calculated from the results measured for 20 arbitrary particles in an arbitrary field of view in a photograph taken by a transmission electron microscope. Similarly, the average particle thickness is calculated from the results measured for 20 arbitrary particles in the same field of view in the photograph taken by the transmission electron microscope.

Examples of the plate-like powder of component (A) include plate-like zinc oxide, plate-like titanium dioxide, plate-like cerium oxide, plate-like barium sulfate, talc, mica, plate-like kaolin, sericite, muscovite, plate-like synthetic mica, phlogopite, lepidolite, biotite, lepidolite, plate-like silicic anhydride, plate-like hydroxyapatite, bentonite, montmorillonite, hectorite, plate-like ceramic powder, plate-like alumina, plate-like boron nitride, plate-like polymethyl methacrylate powder, lauroyl lysine, plate-like iron oxide, titanium dioxide-coated mica, titanium dioxide-treated mica, bismuth oxychloride, titanium dioxide-coated bismuth oxychloride, titanium dioxide-coated talc, scale foil, titanium dioxide-coated colored mica, and aluminum. Among them, from the viewpoint of the ultraviolet ray protective effect, zinc oxide, titanium dioxide, and cerium oxide are preferable. Among them, zinc oxide is more preferable. Furthermore, zinc oxide containing an iron as a trace element is preferable.

As alkylalkoxysilanes used for treating such plate-like powder, an alkylalkoxysilane having a branched or linear alkyl group having 6-20 carbon atoms, preferably 6-10 carbon atoms, and more preferably 8 carbon atoms, and having preferably an alkoxy group having 1-2 carbon atoms and more preferably 2 carbon atoms is preferable. Among these, octyltriethoxysilane and octyltrimethoxysilane are preferable. These compounds can treat the powder more uniformly.

Methods for treating the plate-like powder with alkylalkoxysilane are not limited, and examples of the method include a wet method, a dry method, a vapor deposition method (a method of vapor depositing a treatment agent to a pigment by using plasma and the like), a gas phase method (a method of carrying out surface treatment in a gas such as air and nitrogen), a mechanochemical method (surface treatment is carried out in a mechanochemical manner by using an apparatus such as a ball mill, an angmill (manufactured by Hosokawa Micron Corporation), a hybridizer (manufactured by Nara Machinery Co., Ltd.)), and the like.

Among them, the wet method is a method in which the plate-like powder and the alkylalkoxysilane are mixed with each other in an organic solvent such as lower alcohol, hexane, acetone, toluene, cyclohexane, xylene, dimethylformamide, N-methyl-pyrrolidone, carbon dioxide, and a terpene, and mixing thereof uniformly, followed by removing the organic solvent therefrom by heating or depressurizing, and preferably by heat-treating at 80 to 250° C., is preferred. By employing such a method, the treatment can be performed more uniformly.

The treatment amount of the alkylalkoxysilane is preferably 2 to 10% by weight, and more preferably 2 to 7% by weight with respect to the whole weight of the treated plate-like powder.

One or more types of component (A) may be used, and, in embodiments, component (A) may be included in an amount of 1 to 20% by weight, preferably 3 to 15% by weight, and more preferably 5 to 15% by weight based on a total weight of a cosmetic composition from the viewpoint of formation of a homogeneous coating in combination with component (B) discussed below.

In embodiments, component (B) in cosmetic compositions according to the present invention is an oil that is solid at a temperature of 25° C., and examples thereof include an aliphatic alcohol, a fatty acid, an aliphatic amide derivative, and an aliphatic amine derivative.

Preferable examples of the aliphatic alcohol include a saturated aliphatic alcohol having 12-24 carbon atoms, such as lauryl alcohol, myristyl alcohol, cetanol, stearyl alcohol, and behenyl alcohol. Furthermore, preferable examples of the fatty acid include saturated fatty acid having 12-24 carbon atoms, such as lauric acid, myristic acid, palmitin acid, stearic acid, and behenic acid. Preferable examples of the aliphatic amide derivative include a ceramide such as natural ceramides of type I to type VI, N-(2-hydroxy-3-hexadecyloxypropyl)-N-2-hydroxyethyl hexadecanamide, N-(2-hydroxy-3-hexadecyloxypropyl)-N-2-hydroxyethyl decanamide, and the analogues thereof. Preferable examples of the aliphatic amine derivative include a sphingosine such as sphingosine, dihydrosphingosine, phytosphingosine, dehydrosphingosine, dehydrophytosphingosine, sphingadienine and N-methyl or N,N-dimethyl compounds thereof, and 1-(2-hydroxyethylamino)-3-isostearyloxy-2-propanol. Furthermore, a sterol such as cholesterol, stigmasterol, and ergosterol may be used.

Hydrocarbon-based, ester-based, silicone-based, natural and synthetic waxes may be used. Examples of the wax include animal wax such as beeswax and spermaceti wax; vegetable wax such as carnauba wax, candelilla wax, rice wax, and Japan tallow; mineral wax such as montan wax, ozokerite, ceresin, paraffin wax, and microcrystalline wax; synthetic wax such as polyethylene wax, Fischer-Tropsch wax, a hydrogenated castor oil, a hydrogenated jojoba oil, amide stearate, phthalic anhydride imide, and silicone wax.

In embodiments, component (B) does not include an organic ultraviolet absorber.

Component (B) may form a homogeneous coating on the surface of the skin by bonding with component (A). One or more types of component (B) may be used, and, in embodiments, component (B) may be included in an amount of 0.1 to 10% by weight, preferably 0.1 to 5% by weight, and more preferably 0.5 to 5% by weight based on a total weight of a cosmetic composition from the viewpoint of formation of a coating.

Furthermore, in embodiments of cosmetic compositions according to the present invention, a weight ratio of component (B) to component (A), (B)/(A), is 0.01 to 5, preferably 0.02 to 1, and more preferably 0.1 to 1.

It can be considered that when the weight ratio of component (B) to component (A) is in this range, the size of a water droplet in the W/O emulsified cosmetic composition can be reduced, a uniform and high occlusive coating can be formed on the skin, and therefore a high moisture retaining property can be obtained. It is considered that silicone-treated powder substances and fluorine-treated powder substances, which have been frequently used conventionally, cannot form such a high occlusive coating, causing problems of a feeling to the touch, for example, a problem of dryness.

In embodiments, component (C) in cosmetic compositions according to the present invention is an oil which is in liquid form at 25° C. and has a viscosity at 25° C. of more than 0 and 500,000 mPa·s or less, preferably 100,000 mPa·s or less, and more preferably 5 to 1,000 mPa·s, and which is selected from the group consisting of a hydrocarbon oil, an ester oil and an ether oil.

Viscosity may be measured using a Brookfield (type B) viscometer.

Specific examples of component (C) include a hydrocarbon oil such as liquid paraffin, liquid isoparaffin, hydrogenated polyisobutene, heavy liquid isoparaffin, vaseline, squalane, n-octane, n-heptane, isododecane, and cyclohexane; an ester oil such as diisostearyl malate, octyldodecyl lactate, isotridecyl isononanoate, octyldodecyl myristate, isopropyl palmitate, isopropyl isostearate, butyl stearate, myristyl myristate, isopropyl myristate, octyldodecyl myristate, di-2-ethyl hexyladipate, diisopropyl sebacate, neopentyl glycol dicapric acid, and tricaproin; as well as an ether oil such as dioctyl ether, ethylene glycol monolauryl ether, ethylene glycol dioctyl ether, and glycerol monooleyl ether.

In embodiments, component (C) is free of organic ultraviolet absorbers such as 2-ethyl hexyl paramethoxy cinnamate.

One or more types of component (C) may be used, and, in embodiments, component (C) may be included in an amount of 0.5 to 60% by weight, preferably 0.5 to 40% by weight, and more preferably 5 to 30% by weight based on a total weight of a cosmetic composition from the viewpoint of high conformability to the skin.

Furthermore, in embodiments, a weight ratio of component (B) to component (C), (B)/(C), is 0.0025 to 2, preferably 0.01 to 1, and more preferably 0.1 to 0.2, so that a solubility of component (B) or crystallization of component (B) are appropriately suppressed, furthermore, adhesion to component (A) is enhanced, and thus a high occlusive coating is formed.

In embodiments, component (D) in cosmetic compositions according to the present invention is water. Water may be employed as a balance of the other components, and it is preferable that water is included in amounts of 10 to 60% by weight, and more preferably 20 to 50% by weight based on a total weight of a cosmetic composition so that an excellent moisture retaining property and refreshing effect are achieved.

Furthermore, in embodiments of the present invention, the oil of component (C) is preferably used in combination with component (E), a silicone oil, from the viewpoint of suppressing stickiness at the time of application.

Such silicone oils are preferably, similar to component (C), oils which have a liquid form at 25° C. and have a viscosity at 25° C. of more than 0 and 500,000 mPa·s or less, more preferably 100,000 mPa·s or less, including dimethyl polysiloxane, cyclic dimethyl polysiloxane, methyl phenyl polysiloxane, amino-modified silicone, epoxy-modified silicone, carboxy-modified silicone, alcohol-modified silicone, and alkyl-modified silicone.

Among them, dimethyl polysiloxane and cyclic dimethyl polysiloxane are preferable.

One or more types of component (E) may be used, and, in embodiments, component (E) is preferably included in an amount of 5 to 50% by weight, and more preferably 10 to 40% by weight based on a total weight of a cosmetic composition to achieve a feeling upon use of reduced stickiness.

Furthermore, in embodiments, a total content of components (C) and (E) may be 10 to 80% by weight and further preferably 20 to 60% by weight based on a total weight of a cosmetic composition because an excellent feeling upon use is achieved.

In addition, in embodiments, a weight ratio of component (C) to component (E), (C)/(E), is preferably 0.005 to 5, and more preferably 0.01 to 3 because the formation of a coating composed of components (A) and (B) can be improved and a higher moisture retaining effect can be obtained.

In embodiments, cosmetic compositions according to the present invention may further include component (F), a non-ionic surfactant having HLB of 8 or less, preferably HLB of 4 to 8, and more preferably HLB of 4 to 5. Herein, HLB denotes Hydrophile-Lipophile Balance, and is defined by the following expression from R. Oda, K. Teramura, Synthesis of Surface-Active Agents and Their Application, Makishoten, 1960, p. 501:

$$HLB = (\Sigma \text{ inorganic property value}/\Sigma \text{ organic property value}) \times 10$$

Examples of such a nonionic surfactant include sorbitan fatty acid ester (for example, sorbitan monoisostearate, sorbitan monooleate, sorbitan monopalmitate, sorbitan monostearate, sorbitan sesquioleate, and sorbitan trioleate), glycerin fatty acid ester (for example, glycerin monostearate, glycerin monoisostearate, glycerin distearate, and glycerin monostearate malate), polyglycerin fatty acid ester (for example, diglycerin monostearate, and hexaglycerin tristearate), propylene glycol-pentaerythritol fatty acid ester (for example, propylene glycol monostearate, and pentaerythritol stearate), polyethylene glycol fatty acid ester (for example, POE (4) monostearate and POE (2) monooleate), polyoxyethylene alkyl ether (for example, POE (2) cetyl ether, POE (5) behenyl ether, and POE (3) octyl phenyl ether), polyoxyethylene castor oil-hydrogenated castor oil (for example, POE (3) castor oil, and POE (5) hydrogenated castor oil), modified silicone having a linear, branched, or cross-linked silicone chain (for example, polyether modified silicone, polyether-alkyl comodified silicone, polyglycerin modified silicone, and polyglycerin-alkyl comodified silicone), and sucrose fatty acid ester.

One or more component (F) may be used, and, in embodiments, component (F) may be included in an amount of 0.1 to 20% by weight, preferably 0.5 to 10% by weight, and more preferably 1 to 2.5% by weight based on a total weight of a cosmetic composition from the viewpoint that stability over time of emulsified cosmetic composition, the dispersibility of component (B) in components (C) and (E), and adhesion between components (A) and (B) in the process of application and drying are improved.

In addition, exemplary cosmetic compositions according to the present invention may contain an organic ultraviolet absorber having absorption in the UVA range, so that an ultraviolet ray protective effect and a moisture retaining property can be further enhanced.

As such a compound, oil soluble compounds and water soluble compounds may be used, but oil soluble compounds are more preferable in obtaining the higher effect in the present invention.

Examples of oil soluble ultraviolet absorbers include diethylamino hydroxybenzoyl hexyl benzoate, t-butyl methoxy dibenzoylmethane, and bis-ethylhexyloxy-phenol methoxyphenyl triazine.

Examples of water soluble ultraviolet absorbers include phenylene-1,4-bis-(2-benzimidazyl)-3,3'-5,5'-tetrasulfonic acid and the salt thereof.

One or more types of organic ultraviolet absorber may be used, and, in embodiments, are included preferably in an amount of 0.1 to 10% by weight and more preferably 0.5 to 5% by weight based on a total weight of a cosmetic composition because they can be mixed stably and a sufficient ultraviolet ray protective effect can be obtained.

In particularly preferred embodiments, W/O emulsified cosmetic compositions according to the present invention include components combined in preferred amounts indicated herein.

In a preferred embodiment, a WO emulsified cosmetic composition according to the present invention includes:

(A) 1 to 20% by weight of a plate-like powder that has been surface-treated with an alkylalkoxysilane and which has an average particle diameter of 0.1 to 10 μm;

preferably 1 to 20% by weight of a plate-like powder that has been surface-treated with an alkylalkoxysilane, which has an average particle diameter of 0.1 to 10 μm, and which is selected from the group consisting of zinc oxide, titanium dioxide and selenium oxide, and further preferably 1 to 20% by weight of a plate-like powder that has been surface-treated with octyltriethoxysilane or octyltrimethoxysilane, which has an average particle diameter of 0.1 to 10 μm, and which is selected from the group consisting of zinc oxide, titanium dioxide and selenium oxide;

(B) 0.1 to 10% by weight of an oil that is solid at a temperature of 25° C.;

(C) 0.5 to 60% by weight of an oil selected from the group consisting of a hydrocarbon oil, an ester oil, and an ether oil, having a viscosity at 25° C. of 500,000 mPa·s or less; and (D) water, wherein the weight ratio of component (B) to component (A), (B)/(A), is 0.01 to 5.

In a further preferred embodiment, a W/O emulsified cosmetic composition according to the present invention includes:

(A) 1 to 20% by weight of a plate-like powder that has been surface-treated with an alkylalkoxysilane and which has an average particle diameter of 0.1 to 10 μm;

(B) 0.1 to 10% by weight of an oil that is solid at a temperature of 25° C., selected from the group consisting of a ceramide selected from the group consisting of natural ceramides of type I to type VI, N-(2-hydroxy-3-hexadecyloxypropyl)-N-2-hydroxyethyl hexadecanamide, and N-(2-hydroxy-3-hexadecyloxypropyl)-N-2-hydroxyethyl decanamide and an analogue thereof, as well as a sterol selected from the group consisting of cholesterol, stigmasterol and ergosterol;

(C) 0.5 to 60% by weight of an oil selected from the group consisting of a hydrocarbon oil, an ester oil, and an ether oil, having a viscosity at 25° C. of 500,000 mPa·s or less; and (D) water, wherein the weight ratio of component (B) to component (A), (B)/(A), is 0.01 to 5.

In a further preferred embodiment, a W/O emulsified cosmetic composition according to the present invention includes:

(A) 1 to 20% by weight of a plate-like powder that has been surface-treated with an alkylalkoxysilane and which has an average particle diameter of 0.1 to 10 μm;

(B) 0.1 to 10% by weight of an oil that is solid at a temperature of 25° C.;

(C) 0.5 to 60% by weight of an oil selected from the group consisting of a hydrocarbon oil, an ester oil, and an ether oil, having a viscosity at 25° C. of 500,000 mPa·s or less;

(D) water, and (E) 5 to 50% by weight of a silicone oil, wherein the weight ratio of the component (B) to the component (A), (B)/(A), is 0.01 to 5.

In a further preferred embodiment, a W/O emulsified cosmetic composition according to the present invention includes:

(A) 1 to 20% by weight of a plate-like powder that has been surface-treated with an alkylalkoxysilane and which has an average particle diameter of 0.1 to 10 μm;

(B) 0.1 to 20% by weight of an oil that is solid at a temperature of 25° C.;

(C) 0.5 to 60% by weight of an oil selected from the group consisting of a hydrocarbon oil, an ester oil, and an ether oil, having a viscosity at 25° C. of 500,000 mPa·s or less;

(D) water, (E) 5 to 50% by weight of a silicone oil, and (F) 0.1 to 20% by weight of a nonionic surfactant having HLB of 4 to 8, wherein the weight ratio of the component (B) to the component (A), (B)/(A), is 0.01 to 5.

In a further preferred embodiment, a WO emulsified cosmetic composition according to the present invention includes:

(A) 1 to 20% by weight of a plate-like powder which has been surface-treated with octyltriethoxysilane or octyltrimethoxysilane, which has an average particle diameter of 0.1 to 10 μm, and which is selected from the group consisting of zinc oxide, titanium dioxide and selenium oxide;

(B) 1 to 20% by weight of a ceramide selected from the group consisting of natural ceramides of type I to type VI, N-(2-hydroxy-3-hexadecyloxypropyl)-N-2-hydroxyethyl hexadecanamide, and N-(2-hydroxy-3-hexadecyloxypropyl)-N-2-hydroxyethyl decanamide, and an analogue thereof;

(C) 0.5 to 60% by weight of an oil selected from the group consisting of a hydrocarbon oil and an ester oil, having a viscosity at 25° C. of 500,000 mPa·s or less;

(D) water;

(E) 5 to 50% by weight of dimethyl polysiloxane and cyclic a silicone oil; and (F) 0.1 to 20% by weight of a nonionic surfactant having HLB of 4 to 8, wherein the weight ratio of component (B) to component (A), (B)/(A), is 0.01 to 5.

In a further preferred embodiment, a W/O emulsified cosmetic composition according to the present invention has the following characteristics:

the content of the component (A) is 1 to 20% by weight and preferably 3 to 15% by weight, the content of the component (B) is 0.1 to 10% by weight and preferably 0.1 to 5% by weight, the content of the component (C) is 0.5 to 60% by weight and preferably 0.5 to 40% by weight, the content of the component (D) is the rest of the other components, the content of the component (E) is 5 to 50% by weight and preferably 10 to 40% by weight, the content of the component (F) is 1 to 20% by weight and preferably 0.5 to 10% by weight, the weight ratio by weight of component (B) to component (A), (B)/(A), is 0.01 to 5, preferably 0.02 to 1, the weight ratio of component (B) to component (C), (B)/(C), is 0.0025 to 2, preferably 0.01 to 1, the total content of the components (C) and (E) is 10 to 80% by weight and preferably 20 to 60% by weight, and the weight ratio of component (C) to component (E), (C)/(E), is 0.005 to 5, preferably 0.01 to 3.

In a further preferred embodiment, a W/O emulsified cosmetic composition according to the present invention includes:

(A) 3 to 15% by weight of a plate-like powder that has been surface-treated with an alkylalkoxysilane and which has an average particle diameter of 0.1 to 10 μm;

(B) 0.1 to 5% by weight of an oil that is solid at a temperature of 25° C.;

(C) 0.5 to 40% by weight of an oil selected from the group consisting of a hydrocarbon oil, an ester oil, and an ether oil, having a viscosity at 25° C. of 500,000 mPa·s or less; and (D) water, wherein the weight ratio of component (B) to component (A), (B)/(A), is 0.02 to 1.

In a further preferred embodiment, an W/O emulsified cosmetic composition according to the present invention includes:

(A) 3 to 15% by weight of a plate-like powder that has been surface-treated with an alkylalkoxysilane and which has an average particle diameter of 0.1 to 10 μm;

(B) 0.1 to 5% by weight of an oil that is solid at a temperature of 25° C.;

(C) 0.5 to 60% by weight of an oil selected from the group consisting of a hydrocarbon oil, an ester oil, and an ether oil, having a viscosity at 25° C. of 500,000 mPa·s or less;

(D) water, (E) 10 to 40% by weight of a silicone oil; and (F) 0.5 to 10% by weight of a nonionic surfactant having HLB of 4 to 8, wherein the weight ratio of component (B) to component (A), (B)/(A), is 0.02 to 1.

In a further preferred embodiment, a W/O emulsified cosmetic composition according to the present invention:

(A) 3 to 15% by weight of a plate-like powder that has been surface-treated with an alkylalkoxysilane and which has an average particle diameter of 0.1 to 10 μm;

(B) 0.1 to 5% by weight of an oil that is solid at a temperature of 25° C.;

(C) 0.5 to 60% by weight of an oil selected from the group consisting of a hydrocarbon oil, an ester oil, and an ether oil, having a viscosity at 25° C. of 500,000 mPa·s or less;

(D) water, (E) 10 to 40% by weight of a silicone oil; and (F) 0.5 to 10% by weight of a nonionic surfactant having HLB of 4 to 8, wherein the weight ratio of component (B) to component (A), (B)/(A), is 0.02 to 1, the weight ratio of component (B) to component (C), (B)/(C), is 0.01 to 1, the total content of the components (C) and (E) is 20 to 60% by weight, and the weight ratio of component (C) to component (E), (C)/(E), is 0.01 to 3.

Exemplary cosmetic compositions according to the present invention may contain other components used in usual cosmetic compositions in addition to the above-mentioned components. Examples of the other components include a lower alcohol, a moisturizer, a chelating agent, a whitening agent, a vitamin, other various medical components, powder substances other than the above, ultraviolet absorbers other than the above, antioxidant, perfume, preservative, a pH adjusting agent, a sequestering agent, a sterilizer, and a coloring material.

W/O emulsified cosmetic compositions according to the present invention may be produced according to usual methods.

EXAMPLES

Production Example 1

Production of Plate-Like Zinc Oxide

Into 315 mL of $5 \times 10^{-2}$ mol sulfuric acid aqueous solution, $1.6 \times 10^{-1}$ mol zinc sulfate, $3.8 \times 10^{-2}$ mol sodium sulfate, and $1.6 \times 10^{-4}$ mol ferrous sulfate as a salt of a trace element were dissolved.

And then, while the solution was stirred at 6000 r.p.m. by using a homomixer, 230 mL of 2N aqueous solution of sodium hydroxide were put into the solution for 15 seconds (pH=12.8) to produce a precipitate, and then the solution continued to be stirred for 10 minutes. After that, the solution was subjected to aging at 100° C. for 90 minutes, filtered, washed with water, and dried at 230° C. for about 10 hours to obtain plate-like zinc oxide. The thus obtained powder was observed under a scanning electron microscope to confirm that the powder had flaky particles. The obtained powder had an average particle diameter of 0.25 μm, and a plate ratio of 13.

Production Example 2

Production of Plate-Like Octylsilylated Zinc Oxide

A slurry composed of 93% by weight of the plate-like zinc oxide powder obtained in Production Example 1, 7% by weight of octyltriethoxysilane and toluene was formed, and the slurry was pulverized and cracked by using a bead mill (DYNO-Mill manufactured by Shinmaru Enterprises Corporation). And then, after toluene was evaporated by heating under reduced pressure, the slurry was heat treated at 150° C. for 4 hours by using an air flow type dryer to obtain a plate-like octylsilylated zinc oxide powder.

The thus obtained powder was observed under a scanning electron microscope to confirm that the powder had flaky particles. The obtained powder had an average particle diameter of 0.20 μm, and a plate ratio of 10.

Production Example 3

Production of Plate-Like Silicone-Treated Zinc Oxide

A slurry composed of 98 parts by weight of the plate-like zinc oxide powder obtained in Production Example 1, 2 parts by weight of methyl hydrogen polysiloxane (KF-99P manufactured by Shin-etsu Chemical Co., Ltd.), and isopropyl alcohol was formed. After the slurry was stirred and pulverized, a solvent was evaporated from the slurry by heating under reduced pressure. The slurry was heat treated at 150° C. for 4 hours to obtain a plate-like silicone-treated zinc oxide.

Production Example 4

Production of Octylsilylated Talc

A slurry composed of 98% by weight of a talc powder (FK-500S manufactured by Yamaguchi Mica Co., Ltd.), 2% by weight of octyltriethoxysilane, and toluene was formed, and the slurry was pulverized and cracked by using a bead mill (DYNO-Mill manufactured by Shinmaru Enterprises). And then, toluene was evaporated by heating under reduced pressure, the slurry was heat treated at 150° C. for 4 hours by using an air flow type dryer to obtain an octylsilylated talc powder.

The thus obtained powder was observed under a scanning electron microscope to confirm that the powder was a flaky particle. The obtained powder had an average particle diameter of 10 μm, and a plate ratio of 45.

Examples 1 to 2 and Comparative Examples 1 to 8

W/O emulsified cosmetic compositions having compositions shown in Table 1 were produced according to the following method, and the obtained cosmetic compositions were evaluated for ultraviolet ray protective effect, moisture transpiration rate and degree of dryness. Table 1 also shows the results.

From the results, it is apparent that cosmetic compositions according to the present invention have a high ultraviolet ray protective property, and also have an excellent moisture retaining property by using a plate-like powder that has been surface-treated with an alkylalkoxysilane and an oil that is solid at a temperature of 25° C.

(Production Method)

Component (B), a solid oil, component (C), an oil, component (F), a nonionic surfactant, an ultraviolet absorber, and the like were mixed, and the mixture was dissolved uniformly at 80° C. The obtained oil phase was transferred to an Agi-homomixer, cooled to room temperature, and then, a powder phase obtained by uniformly dispersing the powder of component (A) into a mixture solution of component (E) methyl polysiloxane, N-propionyl polyethylene imine-methyl polysiloxane copolymer and ethanol, was added and stirred. Furthermore, a water phase containing a polyol was added thereto. The mixture was stirred at high speed by using an Agi-homomixer, followed by degassing thereof. Thus, a W/O emulsified cosmetic composition was obtained.

(Evaluation Method)

(1) Ultraviolet Ray Protective Effect:

Each cosmetic composition was applied on a quartz plate at 2 mg/cm$^2$, the total transmitted light spectrum was measured by using a SPF analyzer (manufactured by Optometrics), the protection in a UVB range, the protection in a UVA range, and transparency with respect to visible light were calculated as transmittance in wavelength of 300 nm, 370 nm, and 450 nm, respectively.

(2) Moisture Transpiration Rate (Occlusive Property):

Into a 40 mL-vial bottle, 20 mL of water were added. To a cellulose membrane filter (A300A142C manufactured by Toyo Roshi) having a diameter of 2.2 cm, 0.03 mL of each of the cosmetic compositions was applied, and each filter was placed in a lid having a hole (circle having a diameter of 1.4 cm), and the lid was placed on the vial bottle.

Each vial was stored at a temperature of 30° C. and a humidity of 40% for two days, and the weights before and after storage were measured to calculate the moisture transpiration amount. The moisture transpiration amount when only water was applied to the filter was defined as 100, and the moisture transpiration rate was calculated from the following formula. It was shown that as the calculated value was smaller, the occlusive property of water was higher, and the moisture retaining property was superior.

Moisture transpiration rate (%)=(moisture transpiration amount of sample/moisture transpiration amount of water)×100

(3) Lack Degree of Dryness:

Each of five expert panelists was allowed to carry out function evaluation for the degree of dryness when 1 g each of the cosmetic compositions was applied to the hand, and to determine in five grades from score value 1 to score value 5 in which score value 1 was given when the panelist found much dryness and score value 5 was given when the panelist found no dryness. An arithmetic mean was obtained from the score values, and each of the obtained mean values was rounded off to the nearest integer place to obtain an evaluation value. It was shown that the higher the score was, the greater the degree to which dryness was suppressed.

TABLE 1

| | Component (% by weight) | Example 1 | Comparative Example 1 | Comparative Example 2 | Comparative Example 3 | Comparative Example 4 |
|---|---|---|---|---|---|---|
| A | plate-like octylsilylated zinc oxide (Production Example 2) | 15.0 | | | 15.0 | 15.0 |
| B | N-(hexadecyloxy hydroxy propyl)-N-hydroxyethyl hexadecanamide[*1] | 0.5 | 0.5 | 0.5 | | 0.5 |
| | 2-ethyl hexyl paramethoxy cinnamate[*2] | | | | | |
| | diethylamino hydroxybenzoyl hexyl benzoate[*3] | | | | | |
| C | liquid isoparaffin[*4] | 5.0 | 5.0 | 5.0 | 5.0 | |
| E | methyl cyclopolysiloxane[*6] | 18.0 | 18.0 | 18.0 | 18.0 | 18.0 |
| E | methyl polysiloxane (2 cs)[*7] | 15.3 | 15.3 | 15.3 | 15.8 | 20.3 |
| F | polyoxyethylene-methyl polysiloxane copolymer[*5] | 1.5 | 1.5 | 1.5 | 1.5 | 1.5 |
| | plate-like silicone-treated zinc oxide (Production Example 3) | | 15.0 | | | |
| | octylsilylated zinc oxide fine particle[*8] | | | 15.0 | | |
| | N-propionyl polyethylene imine-methyl polysiloxane copolymer[*9] | 0.2 | 0.2 | 0.2 | 0.2 | 0.2 |
| | ethanol | 0.5 | 0.5 | 0.5 | 0.5 | 0.5 |
| | glycerin | 6.0 | 6.0 | 6.0 | 6.0 | 6.0 |
| D | purified water | balance | balance | balance | balance | balance |
| | Total | 100 | 100 | 100 | 100 | 100 |
| | (B)/(A) | 0.03 | — | — | — | 0.03 |
| | (B)/(C) | 0.1 | 0.1 | 0.1 | — | — |
| | UVB protective effect (T % 300 nm) | 8.85 | 10.9 | 11.3 | 8.62 | 9.34 |
| | UVA protective effect (T % 370 nm) | 8.67 | 9.81 | 13.4 | 8.24 | 9.26 |
| | Transparency (T % 450 nm) | 70.0 | 65.9 | 81.7 | 70.2 | 70.7 |
| | Moisture transpiration rate (%) | 70.2 | 98.9 | 97.1 | 91.5 | 98.0 |
| | Lack degree of dryness | 5 | 2 | 3 | 2 | 1 |

| | Component (% by weight) | Example 2 | Comparative Example 5 | Comparative Example 6 | Comparative Example 7 | Comparative Example 8 |
|---|---|---|---|---|---|---|
| A | plate-like octylsilylated zinc oxide (Production Example 2) | 15.0 | | | 15.0 | 15.0 |
| B | N-(hexadecyloxy hydroxy propyl)-N-hydroxyethyl hexadecanamide[*1] | 0.5 | 0.5 | 0.5 | | 0.5 |
| | 2-ethyl hexyl paramethoxy cinnamate[*2] | 3.0 | 3.0 | 3.0 | 3.0 | 3.0 |
| | diethylamino hydroxybenzoyl hexyl benzoate[*3] | 1.0 | 1.0 | 1.0 | 1.0 | 1.0 |
| C | liquid isoparaffin[*4] | 5.0 | 5.0 | 5.0 | 5.0 | |
| E | methyl cyclopolysiloxane[*6] | 18.0 | 18.0 | 18.0 | 18.0 | 18.0 |
| E | methyl polysiloxane (2 cs)[*7] | 11.3 | 11.3 | 11.3 | 11.8 | 16.3 |
| F | polyoxyethylene-methyl polysiloxane copolymer[*5] | 1.5 | 1.5 | 1.5 | 1.5 | 1.5 |
| | plate-like silicone-treated zinc oxide (Production Example 3) | | 15.0 | | | |
| | octylsilylated zinc oxide fine particle[*8] | | | 15.0 | | |
| | N-propionyl polyethylene imine-methyl polysiloxane copolymer[*9] | 0.2 | 0.2 | 0.2 | 0.2 | 0.2 |
| | ethanol | 0.5 | 0.5 | 0.5 | 0.5 | 0.5 |

TABLE 1-continued

|   |   |   |   |   |   |   |
|---|---|---|---|---|---|---|
|   | glycerin | 6.0 | 6.0 | 6.0 | 6.0 | 6.0 |
| D | purified water | balance | balance | balance | balance | balance |
|   | Total | 100 | 100 | 100 | 100 | 100 |
|   | (B)/(A) | 0.03 | — | — | — | 0.03 |
|   | (B)/(C) | 0.1 | 0.1 | 0.1 | — | — |
|   | UVB protective effect (T % 300 nm) | 2.15 | 2.13 | 1.95 | 2.14 | 1.91 |
|   | UVA protective effect (T % 370 nm) | 6.55 | 7.83 | 10.6 | 7.81 | 8.39 |
|   | Transparency (T % 450 nm) | 73.2 | 66.9 | 82.4 | 74.8 | 71.5 |
|   | Moisture transpiration rate (%) | 57.3 | 98.0 | 99.3 | 90.5 | 99.3 |
|   | Lack degree of dryness | 5 | 3 | 3 | 3 | 2 |

[1] Sofcare Ceramide SLE (manufactured by Kao Corporation)
[2] Uvinul MC80 (manufactured by BASF)
[3] Uvinul A Plus (manufactured by BASF)
[4] ParLeam Ex (manufactured by NOF CORPORATION)
[5] Silicone SH3775M (manufactured by Dow Corning Toray Co., Ltd.; HLB5)
[6] Silicone TSF405A (manufactured by Momentive Performance Materials Inc.)
[7] Silicone KF-96L-2CS (manufactured by Shin-Etsu Silicone Co., Ltd.)
[8] Powder obtained by octylsilyl-treating the surface of zinc oxide ZnO-350 fine particle (manufactured by Sumitomo Osaka Cement Co., Ltd.)
[9] POLYSILICONE-9 (INCI name manufactured by Kao Corporation)

Examples 3 to 8

W/O emulsified cosmetic compositions having the compositions shown in Table 2 were produced in the same manner as in Examples 1 and 2, and the obtained cosmetic compositions were evaluated in terms of moisture transpiration rate and degree of dryness. Table 2 also shows the results thereof.

Furthermore, the obtained cosmetic compositions had excellent transparency and a high ultraviolet ray protective effect.

TABLE 2

|   | Component (% by weight) | Example 3 | Example 4 | Example 5 | Example 6 | Example 7 | Example 8 |
|---|---|---|---|---|---|---|---|
| A | plate-like octylsilylated zinc oxide (Production Example 2) | 1 | 20 | 10 | 1 | 20 | 3 |
| B | N-(hexadecyloxy hydroxy propyl)-N-hydroxyethyl hexadecanamide[1] |   | 1.4 | 0.1 | 5 | 0.4 | 10 |
| B | cholesterol[10] | 1 |   |   |   |   |   |
|   | diethylamino hydroxybenzoyl hexyl benzoate[3] |   | 1 |   |   |   | 3 |
|   | 2-ethyl hexyl paramethoxy cinnamate[2] | 3 | 3 |   | 3 | 3 | 6 |
| C | liquid isoparaffin[4] | 8 | 10 | 0.5 | 10 | 10 | 10 |
| C | isododecane[11] |   |   |   | 10 | 10 |   |
| C | hydrogenated polyisobutene[12] |   |   |   |   | 10 |   |
| C | isotridecyl isononanoate[13] |   |   |   | 10 | 10 |   |
| E | methyl cyclopolysiloxane[6] | 20 | 30 | 30 |   |   | 10 |
| E | methyl polysiloxane (2 cs)[7] | 20 | 20 | 20 | 10 | 5 |   |
| F | polyoxyethylene-methyl polysiloxane copolymer[14] |   |   |   | 1 | 8 | 0.5 |
| F | polyoxyethylene-methyl polysiloxane copolymer[5] | 1.5 | 0.5 | 1.5 | 2 |   | 2.5 |
| F | polyoxyethylene cetyl ether[15] |   |   |   |   | 2 |   |
|   | dextrin palmitate[16] |   |   |   |   |   | 0.5 |
|   | plate-like silicone-treated zinc oxide (Production Example 3) | 1 |   |   | 5 |   | 1 |
|   | silicone-treated zinc oxide fine particle[8] | 13 |   |   | 4 |   | 1 |
|   | N-propionyl polyethylene imine - methyl polysiloxane copolymer[9] | 0.2 | 0.2 | 0.2 | 0.2 | 0.2 |   |
|   | ethanol | 0.5 | 0.5 | 0.5 | 0.5 | 0.5 | 0.5 |
|   | glycerin | 6 | 6 | 6 | 6 | 13.9 | 10.3 |
|   | magnesium sulfate |   |   |   |   |   | 0.7 |
| D | purified water | balance | balance | balance | balance | balance | balance |
|   | Total | 100 | 100 | 100 | 100 | 100 | 100 |
|   | (B)/(A) | 1.0 | 0.07 | 0.01 | 5.0 | 0.02 | 3.3 |
|   | (B)/(C) | 0.13 | 0.14 | 0.2 | 0.17 | 0.01 | 1.0 |
|   | Moisture transpiration rate (%) | 75.0 | 58.4 | 80.7 | 47.2 | 54.5 | 51.2 |
|   | Lack degree of dryness | 5 | 5 | 5 | 5 | 5 | 5 |

TABLE 3

| | | |
|---|---|---|
| *10: | Cholesterol (JSCI) (manufactured by Nippon Fine Chemical Co., Ltd.) | |
| *11: | MARCASOL R (manufactured by Maruzen Petrochemical Co., Ltd.) | |
| *12: | IP Solvent 1620MU (manufactured by IDEMITSU KOSAN CO., LTD.) | |
| *13: | Salacos 913 (manufactured by The Nisshin OilliO Group, Ltd.) | |
| *14: | Silicone KF-6015 (manufactured by Shin-Etsu Silicone Co,. Ltd.; HLB4) | |
| *15: | Nikkol BC-2 (manufactured by Nikko Chemicals Co., Ltd.; HLB8) | |
| *16: | Rheopearl KL2 (manufactured by Chiba Flour Milling Co., Ltd.) | |

Examples 9 to 14

W/O emulsified cosmetic compositions having the following compositions were produced in the same manner as in Examples 1 and 2.

The obtained cosmetic compositions had an excellent ultraviolet ray protective effect and a high moisture retaining property.

TABLE 4

Example 9

| (Component) | (% by weight) |
|---|---|
| N-(hexadecyloxy hydroxy propyl)-N-hydroxyethyl hexadecanamide (Sofcare Ceramide SLE manufactured by Kao Corporation) | 0.5 |
| 2-ethyl hexyl paramethoxy cinnamate (Uvinul MC80 manufactured by BASF) | 3.0 |
| t-butyl methoxy dibenzoylmethane (Parsol 1789 manufactured by DSM Nutrition Japan) | 0.5 |
| bis-ethylhexyloxy-phenol methoxyphenyl triazine (Tinosorb S manufactured by Ciba Specialty Chemicals Corporation) | 0.5 |
| liquid isoparaffin (ParLeam Ex manufactured by NOF CORPORATION) | 0.5 |
| polyoxyethylene-methyl polysiloxane copolymer (Silicone SH3775M manufactured by Dow Corning Toray Co., Ltd.; HLB5) | 1.5 |
| methyl cyclopolysiloxane (Silicone TSF405A manufactured by Momentive Performance Materials Inc.) | 18.0 |
| methyl polysiloxane (2cs) (Silicone KF-96L-2CS manufactured by Shin-Etsu Silicone Co,. Ltd.) | 10.0 |
| methyl polysiloxane (6cs) (Silicone KF-96L-6CS manufactured by Shin-Etsu Silicone Co,. Ltd.) | 5.0 |
| plate-like octylsilylated zinc oxide (Production Example 2) | 15.0 |
| silicone-coated talc (silicone-coated with Talc JA-46R (manufactured by ASADA MILLING CO., LTD.)) | 3.0 |
| N-propionyl polyethylene imine-methyl polysiloxane copolymer (POLYSILICONE-9, INCI name, manufactured by Kao Corporation) | 0.2 |
| ethanol | 3.5 |
| glycerin | 6.0 |
| purified water | balance |
| Total | 100 |

((B)/(A) = 0.03)

TABLE 5

Example 10

| (Component) | (% by weight) |
|---|---|
| N-(hexadecyloxy hydroxy propyl)-N-hydroxyethyl hexadecanamide (Sofcare Ceramide SLE manufactured by Kao Corporation) | 0.5 |
| 2-ethyl hexyl paramethoxy cinnamate (Uvinul MC80 manufactured by BASF) | 3.0 |
| diethylamino hydroxybenzoyl hexyl benzoate (Uvinul A Plus manufactured by BASF) | 0.5 |
| liquid isoparaffin (ParLeam Ex manufactured by NOF CORPORATION) | 0.5 |
| polyoxyethylene-methyl polysiloxane copolymer (Silicone SH3775M manufactured by Dow Corning Toray Co., Ltd.; HLB5) | 1.5 |
| methyl cyclopolysiloxane (Silicone TSF405A manufactured by Momentive Performance Materials Inc.) | 18.3 |
| methyl polysiloxane (2cs) (Silicone KF-96L-2CS manufactured by Shin-Etsu Silicone Co,. Ltd.) | 10.0 |
| methyl polysiloxane (6cs) (Silicone KF-96L-6CS manufactured by Shin-Etsu Silicone Co,. Ltd.) | 5.0 |
| plate-like octylsilylated zinc oxide (Production Example 2) | 5.0 |
| silicone-coated zinc oxide fine particle (powder substance obtained by coating the surface of zinc oxide MZ500 fine particle (manufactured by TAYCA CORPORATION) with silicone) | 10.0 |
| silicone-coated talc (silicone-coated Talc JA-46R (manufactured by ASADA MILLING CO., LTD.)) | 3.0 |
| N-propionyl polyethylene imine-methyl polysiloxane copolymer (POLYSILICONE-9, INCI name, manufactured by Kao Corporation) | 0.2 |
| ethanol | 3.5 |
| glycerin | 6.0 |
| purified water | balance |
| Total | 100 |

((B)/(A) = 0.1)

TABLE 6

Example 11

| (Component) | (% by weight) |
|---|---|
| N-(hexadecyloxy hydroxy propyl)-N-hydroxyethyl hexadecanamide (Sofcare Ceramide SLE manufactured by Kao Corporation) | 1.0 |
| 2-ethyl hexyl paramethoxy cinnamate (Uvinul MC80 manufactured by BASF) | 4.0 |
| diethylamino hydroxybenzoyl hexyl benzoate (Uvinul A Plus manufactured by BASF) | 0.5 |
| squalane | 10.0 |
| neopentyl glycol dicapric acid (Estemol N-01 manufactured by The Nisshin OilliO Group, Ltd.) | 5.0 |
| isotridecyl isononanoate (Salacos 913 manufactured by The Nisshin OilliO Group, Ltd.) | 5.0 |
| hydrogenated polyisobutene (IP Solvent 2028 manufactured by IDEMITSU KOSAN CO., LTD.) | 10.0 |
| sorbitan stearate (RHEODOL SP-S10V manufactured by Kao Corporation; HLB4.7) | 0.1 |
| Polyoxyethylene-methyl polysiloxane copolymer (Silicone SH3775M manufactured by Dow Corning Toray Co., Ltd.; HLB5) | 3.0 |

TABLE 6-continued

Example 11

| (Component) | (% by weight) |
|---|---|
| methyl polysiloxane (2cs) (Silicone KF-96L-2CS manufactured by Shin-Etsu Silicone Co,. Ltd.) | 10.0 |
| methyl polysiloxane (6cs) (Silicone KF-96L-6CS manufactured by Shin-Etsu Silicone Co,. Ltd.) | 3.0 |
| plate-like octylsilylated zinc oxide (Production Example 2) | 10.0 |
| silicone-coated talc (silicone-coated Talc JA-46R (manufactured by ASADA MILLING CO., LTD.)) | 3.0 |
| N-propionyl polyethylene imine-methyl polysiloxane copolymer (POLYSILICONE-9, INCI name, manufactured by Kao Corporation) | 0.6 |
| ethanol | 1.4 |
| glycerin | 13.0 |
| purified water | balance |
| Total | 100 |

((B)/(A) = 0.1)

TABLE 7

Example 12

| (Component) | (% by weight) |
|---|---|
| N-(hexadecyloxy hydroxy propyl)-N-hydroxyethyl hexadecanamide (Sofcare Ceramide SLE manufactured by Kao Corporation) | 0.5 |
| 2-ethyl hexyl paramethoxy cinnamate (Uvinul MC80 manufactured by BASF) | 3.0 |
| diethylamino hydroxybenzoyl hexyl benzoate (Uvinul A Plus manufactured by BASF) | 1.0 |
| liquid isoparaffin (ParLeam Ex manufactured by NOF CORPORATION) | 0.5 |
| polyoxyethylene-methyl polysiloxane copolymer (Silicone SH3775M manufactured by Dow Corning Toray Co., Ltd.; HLB5) | 1.0 |
| methyl cyclopolysiloxane (Silicone TSF405A manufactured by Momentive Performance Materials Inc.)) | 18.3 |
| methyl polysiloxane (2cs) (Silicone KF-96L-2CS manufactured by Shin-Etsu Silicone Co,. Ltd.) | 10.0 |
| methyl polysiloxane (6cs) (Silicone KF-96L-6CS manufactured by Shin-Etsu Silicone Co,. Ltd.) | 5.0 |
| silicone-coated zinc oxide fine particle (powder substance obtained by coating the surface of zinc oxide MZ500 fine particle (manufactured by TAYCA CORPORATION) with silicone) | 3.0 |
| octylsilylated talc (Production Example 4) | 10.0 |
| N-propionyl polyethylene imine-methyl polysiloxane copolymer (POLYSILICONE-9, INCI name, manufactured by Kao Corporation) | 0.2 |
| ethanol | 0.5 |
| glycerin | 6.0 |
| purified water | balance |
| Total | 100 |

((B)/(A) = 0.05)

TABLE 8

Example 13

| (Component) | (% by weight) |
|---|---|
| N-(hexadecyloxy hydroxy propyl)-N-hydroxyethyl hexadecanamide (Sofcare Ceramide SLE manufactured by Kao Corporation) | 3.0 |
| 2-ethyl hexyl paramethoxy cinnamate (Uvinul MC80 manufactured by BASF) | 3.0 |
| diethylamino hydroxybenzoyl hexyl benzoate (Uvinul A Plus manufactured by BASF) | 0.5 |
| cholesteryl isostearate (EXCEPARL IS-CE-A manufactured by Kao Corporation) | 0.2 |
| dextrin palmitate (Rheopearl KL2 manufactured by Chiba Flour Milling Co., Ltd.) | 0.3 |
| liquid isoparaffin (ParLeam Ex manufactured by NOF CORPORATION) | 0.5 |
| squalane | 0.5 |
| neopentyl glycol dicapric acid (Estemol N-01 manufactured by The Nisshin OilliO Group, Ltd.) | 2.0 |
| polyoxyethylene-methyl polysiloxane copolymer (Silicone SH3775M manufactured by Dow Corning Toray Co., Ltd.; HLB5) | 2.5 |
| methyl cyclopolysiloxane (Silicone TSF405A manufactured by Momentive Performance Materials Inc.) | 17.6 |
| methyl polysiloxane (6cs) (Silicone KF-96L-6CS manufactured by Shin-Etsu Silicone Co,. Ltd.) | 9.0 |
| plate-like octylsilylated zinc oxide (Production Example 2) | 4.0 |
| silicone-coated zinc oxide fine particle (powder substance obtained by coating the surface of zinc oxide MZ500 fine particle (manufactured by TAYCA CORPORATION) with silicone) | 6.0 |
| N-propionyl polyethylene imine-methyl polysiloxane copolymer (POLYSILICONE-9, INCI name, manufactured by Kao Corporation) | 0.9 |
| magnesium sulfate | 1.0 |
| ethanol | 4.5 |
| glycerin | 17.0 |
| purified water | balance |
| Total | 100 |

((B)/(A) = 0.75)

TABLE 9

Example 14

| (Component) | (% by weight) |
|---|---|
| N-(hexadecyloxy hydroxy propyl)-N-hydroxyethyl hexadecanamide (Sofcare Ceramide SLE manufactured by Kao Corporation) | 0.5 |
| 2-ethyl hexyl paramethoxy cinnamate (Uvinul MC80 manufactured by BASF) | 3.0 |
| liquid isoparaffin (ParLeam Ex manufactured by NOF CORPORATION) | 5.0 |
| Isododecane (MARCASOL R manufactured by Maruzen Petrochemical Co., Ltd.) | 10.0 |
| isotridecyl isononanoate (Salacos 913 manufactured by The Nisshin OilliO Group, Ltd.) | 10.0 |
| polyoxyethylene-methyl polysiloxane copolymer (Silicone SH3775M manufactured by Dow Corning Toray Co., Ltd.; HLB5) | 1.5 |
| plate-like octylsilylated zinc oxide (Production Example 2) | 5.0 |
| silicone-coated zinc oxide fine particle (powder substance obtained by coating the surface of | 5.0 |

TABLE 9-continued

Example 14

| (Component) | (% by weight) |
|---|---|
| zinc oxide MZ500 fine particle (manufactured by TAYCA CORPORATION) with silicone | |
| silicone-coated talc | 3.0 |
| (silicone-coated Talc JA-46R (manufactured by ASADA MILLING CO., LTD.)) | |
| N-propionyl polyethylene imine-methyl polysiloxane copolymer | 0.2 |
| (POLYSILICONE-9, INCI name, manufactured by Kao Corporation) | |
| ethanol | 3.5 |
| glycerin | 6.0 |
| purified water | balance |
| Total | 100 |

((B)/(A) = 0.1)

The invention claimed is:

1. A W/O emulsified cosmetic composition comprising the following components (A), (B), (C), (D), (E), and (F):
(A) 1 to 20% by weight of a plate-like powder selected from the group consisting of octylsilylated zinc oxide and octylsilylated talc;
(B) 0.1 to 10% by weight of N-(hexadecyloxy hydroxyl propyl)-N-hydroxyethyl hexadecanamide;
(C) 0.5 to 60% by weight of an oil selected from the group consisting of liquid isoparaffin, isododecane, hydrogenated polyisobutene, isotridecyl isononanoate, squalane, diisostearyl malate, and neopentyl glycol dicapric acid; and
(D) water,
E) a silicone oil selected from the group consisting of methyl cyclopolysiloxane and methyl polysiloxane (2cs); and
(F) a nonionic surfactant selected from the group consisting of polyoxyethylene-methyl polysiloxane copolymer and polyoxyethylene cetyl ether;
wherein:
a ratio by weight of the component (B) to the component (A) satisfies (B)/(A)=0.01 to 5; and
the composition is the form of a W/O emulsion.

2. The composition according to claim 1, wherein the plate-like powder (A) has an average particle diameter of 0.1 to 10 μm.

3. The composition according to claim 1, wherein a weight ratio of (B) to (C), (B)/(C), is 0.0025 to 2.

4. The composition according to claim 1, wherein a total content of the components (C) and (E) is 10 to 80% by weight.

5. The composition according to of claim 1, wherein a weight ratio of the component (C) to the component (E), (C)/(E), is 0.005 to 5.

6. The composition according to claim 1, further comprising an organic ultraviolet absorber having an absorption in an UVA range.

7. The composition according to claim 1, wherein the plate-like powder (A) is octylsilylated zinc oxide.

8. The composition according to claim 1, wherein the plate-like powder (A) is octylsilylated talc.

9. The composition according to claim 1, wherein the oil (C) comprises liquid isoparaffin.

10. The composition according to claim 1, wherein the oil (C) comprises squalane.

11. The composition according to claim 1, wherein the oil (C) comprises diisostearyl malate.

12. The composition according to claim 1, wherein the oil (C) comprises neopentyl glycol dicapric acid.

13. The composition according to claim 1, wherein the silicone oil (E) comprises methyl cyclopolysiloxane.

14. The composition according to claim 1, wherein the silicone oil (E) comprises methyl polysiloxane (2cs).

15. The composition according to claim 1, wherein the nonionic surfactant (F) comprises polyoxyethylene-methyl polysiloxane copolymer.

16. The composition according to claim 1, wherein the nonionic surfactant (F) comprises polyoxyethylene cetyl ether.

17. The composition according to claim 1, wherein the oil (C) is present in the composition in an amount of 0.5 to 40% by weight.

18. The composition according to claim 1, wherein the silicone oil (E) is present in the composition in an amount of 5 to 50% by weight.

19. The composition according to claim 1, wherein the nonionic surfactant (F) is present in the composition in an amount of 0.1 to 20% by weight.

20. A method of moisturizing skin, comprising:
applying the composition according to claim 1 to the skin; and
retaining the composition on the skin.

* * * * *